United States Patent [19]

Andersson

[11] Patent Number: 4,471,504

[45] Date of Patent: Sep. 18, 1984

[54] TOOTHBRUSH

[76] Inventor: Bengt Andersson, Östra Farmvägen 42 D, S-214 41 Malmö, Sweden

[21] Appl. No.: 457,642

[22] Filed: Jan. 13, 1983

Related U.S. Application Data

[63] Continuation of Ser. No. 227,070, Jul. 8, 1980, abandoned.

[30] Foreign Application Priority Data

Nov. 9, 1978 [WO] Int'l Appl. .......... PCT/SE-78/0072

[51] Int. Cl.³ ............................................. A46B 13/02
[52] U.S. Cl. ........................................ 15/22 R; 15/23
[58] Field of Search ................ 15/22 R, 22 A, 22 C, 15/23, 24; 128/62 R

[56] References Cited

U.S. PATENT DOCUMENTS

| 1,795,098 | 3/1931 | Scadding | 15/23 |
| 3,270,360 | 9/1966 | Kropp | 15/22 R |
| 3,284,829 | 11/1966 | Allen | 15/22 R |
| 3,451,086 | 6/1969 | Burgett | 15/23 |
| 3,661,018 | 5/1972 | Keefer | 15/22 R |
| 4,084,280 | 4/1978 | May | 15/22 R |

Primary Examiner—Edward L. Roberts
Attorney, Agent, or Firm—Brumbaugh, Graves, Donohue & Raymond

[57] ABSTRACT

A toothbrush has a cylindrical bristle-carrying head (4; 26) which is rotatable about its longitudinal axis and at the same time reciprocatory along its longitudinal axis by the rotation of a rotor (6; 10) arranged on the handle of the toothbrush. In one embodiment, the toothbrush has means (29, 29a, 30, 30a) which, for ensuring the desired direction of rotation of the brush head, are adapted to block against rotation in the opposite direction.

7 Claims, 9 Drawing Figures

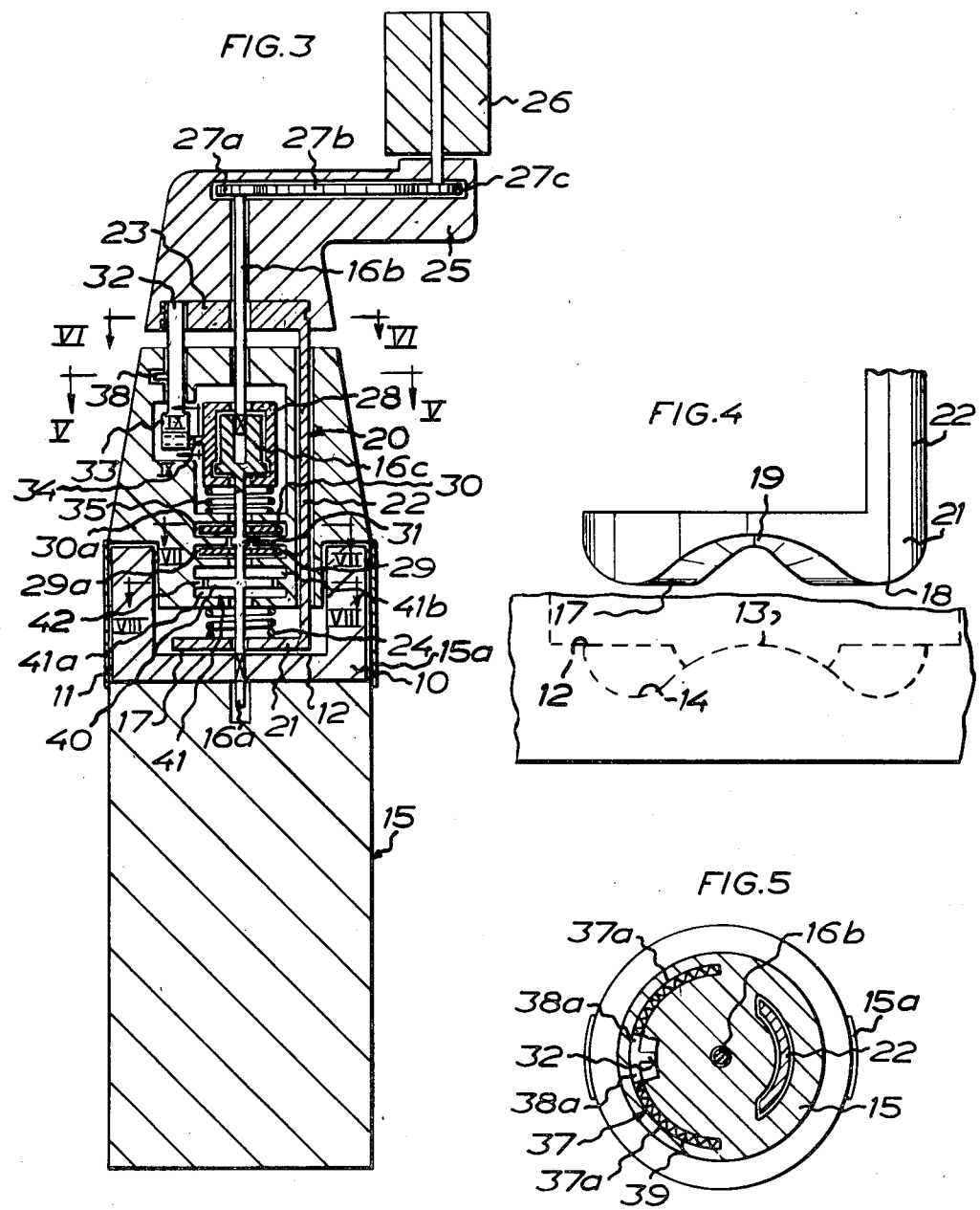

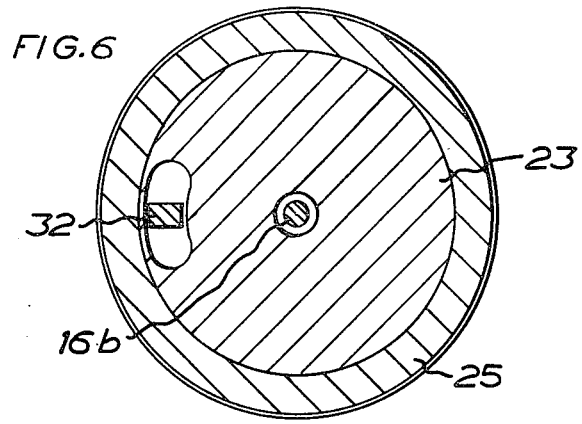
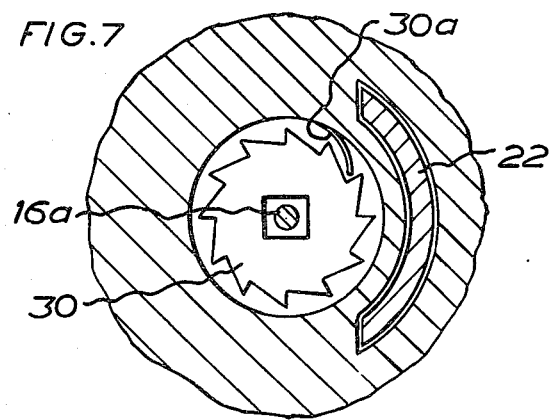
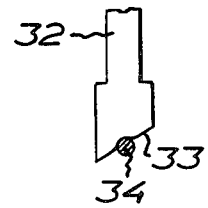
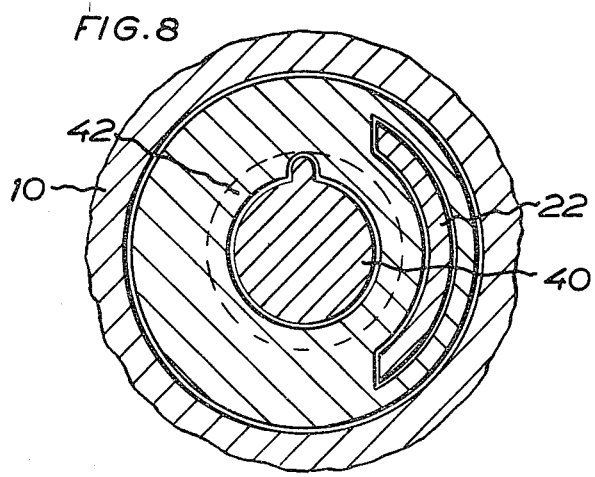

TOOTHBRUSH

This is a continuation of application Ser. No. 227,070, filed July 8, 1980, now abandoned.

TECHNICAL FIELD

The present invention relates to a toothbrush.

BACKGROUND OF THE INVENTION

Dental care is constantly subjected to intensive research and development work. Research and development in the design and the handling of the toothbrushes are a focus of attention. Different methods of toothbrushing have been proposed and put into practice, such as rotary sweeping in the longitudinal direction of the teeth and rubbing in the transverse direction of the teeth, and a combination of rotation and rubbing. The last-mentioned combination is the most recommended method, but it is also the most complicated and time-consuming if it is carried out correctly with conventional toothbrushes having a flat head from one side of which the bristles project. In fact, with such brushes it becomes necessary to perform the rotational operation and the rubbing operation alternatingly with complicated twistings and adjustments of the hand and of the arm.

SUMMARY OF THE INVENTION

The object of the invention is to provide a toothbrush which substantially simplifies the toothbrushing operation and which allows the user simultaneously to perform brushing of the teeth and of the gums in the longitudinal direction of the teeth and in the transverse direction of the teeth.

According to the invention, this object is achieved by means of a toothbrush having the features stated in one or more of the claims.

BRIEF DESCRIPTION OF THE DRAWINGS

The invention will be described in greater detail hereinbelow with reference to the accompanying drawings.

FIG. 3 is a longitudinal section of a second embodiment of the invention,

FIG. 4 illustrates cooperating ondulatory surfaces of the embodiment of FIG. 3 in lateral perspective view, FIG. 5 is a section 5—5 in FIG. 3, FIG. 6 is a cross-sectional view taken along line 6—6 of FIG. 3, FIG. 7 is a cross-sectional view taken along line 7—7 of FIG. 3, FIG. 8 is a cross-sectional view taken along line 8—8 of FIG. 3, and FIG. 9 is a cross-sectional view taken along line 9—9 of FIG. 3.

DETAILED DESCRIPTION OF THE PREFERRED EMBODIMENTS

Figure 1:
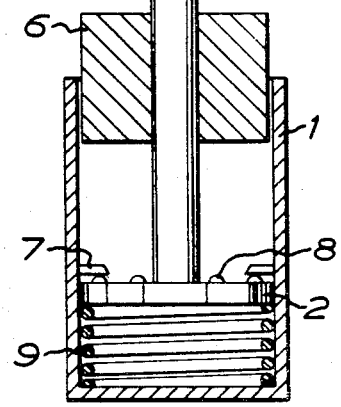
FIG. 1 shows one embodiment of the invention in longitudinal section.
Figure 2:
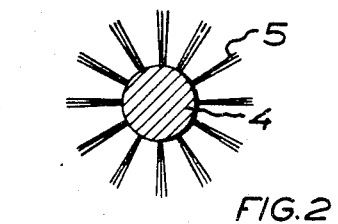
FIG. 2 is a section along the line 2—2 in FIG. 1.

Reference is now made to FIG. 1, showing slightly schematically a simple embodiment of a toothbrush according to the invention. A hollow housing 1 which has an inner circular cylindrical boundary wall and which forms the handle of a toothbrush, accommodates a piston 2 adapted for rotation in opposite directions about its axis and for reciprocation along its axis, the piston being fixed to a shaft 3 which protrudes from the housing and, on its free end, carries a brush head 4. The bristles 5 fixed on the brush head project radially from the brush head in axial equidistant groups (FIG. 2).

To permit rotation of the brush head, a rotor 6 fixedly connected to the shaft and rotatably mounted in the housing, projects from the housing. On the inner side of the housing, there are mounted two cams 7 which are disposed oppposite each other and which, as the rotor rotates, cam over equidistant cam followers 8 provided on the upper side of the piston which rotates along with the rotor. The cam followers have a gentle rise and slope, respectively, on either side of a top, for unimpeded rotation of the rotor and of the brush head connected to it. A compression spring 9 is disposed between the lower side of the piston and the bottom of the housing for reciprocating movement of the piston and the brush head.

During the toothbrushing operation, the toothbrush is held in horizontal position (it is shown in vertical position in FIG. 1) and the rotor 6 is turned by the user's fingers in the desired direction, the brush sweeping over the tooth and gum surfaces in a rotational movement while at the same time performing a reciprocating movement in its longitudinal direction.

Reference will now be had to FIG. 3. A cup-shaped operating rotor member 10 with a side wall 11 and an inner annular bottom surface 12 which in the circumferential direction has successive wave crests 13 and troughs 14 (cf. FIG. 4 showing this surface in perspective), is rotatably mounted in a housing 15, the member 10 being retained against transverse movement with respect to the longitudinal direction of the housing by means of a shaft 16a and two diametrically opposite narrow strips 15a of the material of the housing which are integral therewith. Thus, while the strips 15a retain the member 10 captive within the housing 15, member 10 can rotate with respect to housing 15. The surface 12 cooperates with an annular surface 17 with wave crests 18 and troughs 19 (FIG. 4) on a reciprocating means 20 which is longitudinally slidable in the housing 15 and consists of an annular portion 21 whose lower side comprises the surface 17, an approximately semiannular portion 22 and an annular bearing portion 23. The shaft 16a has a lower portion of profiled, for instance hexagonal, cross-section, and the operating member 10 similarly has a profiled boundary wall for its inner opening, such that the shaft 16a rotates with the operating member 10 but is slidable in its longitudinal direction in the operating member 10. Above said shaft portion, the shaft 16a has a portion of such cross-section, for instance circular, that the shaft can rotate freely with respect to the reciprocating means 20. When the operating member 10 is turned by the fingers of the user, for e.g., the crests and the troughs 13, 14 of the surface 12 will cam over the crests and troughs 18, 19 on the surface 17 of the reciprocating means 20, so that this means will reciprocate, i.e. moves back and forth (upwards and downwards in FIG. 3) as at the same time the shaft 16a rotates. Since FIG. 3 is a cross-sectional view, it does not show the crests and troughs 13, 14, 18 and 19 which are shown in FIG. 4. To ensure positive reciprocation, a spring 24 is arranged between a portion of the housing and the portion 21 of the reciprocating means 20. The bearing portion 23 of the reciprocating means 20 is connected to a holder 25 for a cylindrical toothbrush head 26 of the embodiment shown in FIGS. 1 and 2, such that the holder 25 will reciprocate together with the reciprocating means 20. The brush head holder 25 contains a toothed disk/toothed belt transmission with toothed wheels 27a, 27c and a toothed belt 27b, the toothed wheel 27c being connected to the toothbrush head 26 for co-rotation therewith and the toothed wheel 27a being connected to a shaft 16b which is connected to the shaft 16a but is separated therefrom in the longitudinal direction. The connection between the shafts 16a and 16b is such that these shafts are rotatable as a unit but are movable in the longitudinal direction towards and from each other. The bearing portion 23 on the reciprocating means 20 has such a defining wall for its inner opening that such co-rotation and such relative movement are allowed.

Said connection between the shafts 16a and 16b is ensured by means of a cylindrical member 28 which is mounted in the housing only for longitudinal sliding movement therein and which, in turn, internally holds a rotary hollow sleeve 16c which is connected to the shaft 16a and which, for longitudinal sliding movement but for co-rotation receives the shaft 16b, which is ensured by means of a profiled, for instance hexagonal, cross-section of a portion of the shaft 16b that is received in the sleeve 16c, with a corresponding profile of the inner opening of the sleeve 16c.

The toothed wheels 27a, 27c and the toothed belt 27b are mounted in an appropriate recess in the holder 25, such that, when the operating member 10 is turned, the shafts 16a, 16b which may thus be considered as a single shaft 16, will rotate and, by the intermediary of the transmission 27a-27c, also the brush head 26 which at the same time reciprocates by the intermediary of the reciprocating means 20 and the brush head holder 25 connected thereto, the shafts 16a and 16b moving towards and from each other.

Shaft portion 16a and rotor 10 are engaged for co-rotation, but are allowed to move longitudinally with respect to each other. Shaft portion 16a and reciprocating means 20 can rotate freely with respect to each other.

It should be noted that said portions of the shafts 16a, 16b and the coupling sleeve 16c have such a longitudinal extent that the shafts 16a, 16b and thus the toothbrush head 26, as above, can perform full revolutions in an optional direction of rotation and during these full revolutions, can perform a number of reciprocating movements or strokes, this number being determined by the number of cooperating wave crests and wave troughs 13, 14, 18, 19.

With the hitherto described details, the embodiment of the toothbrush according to the invention shown in FIG. 3 has the same function as the embodiment described in connection with FIG. 1, but also another important feature according to the invention, with a view to ensuring more efficient tooth-brushing, i.e. the longitudinal axis of the cylindrical toothbrush head 26 is offset with respect to the longitudinal axis of the toothbrush handle comprising the housing 15 in its lower portion and the brush holder 25 in its upper portion. This is achieved in that the brush head is disposed on the free end of a portion of the brush holder 25 which laterally projects either obliquely or normally, the longitudinal axis of the brush head 26 preferably being parallel to the longitudinal direction of said handle. By said lateral offset, the longitudinal axis of the brush head, when the handle is held horizontal with respect to the row of teeth to be brushed, can always be applied against the teeth in parallel with the edge of the gums, such that the bristles over the entire surface of the brush head that faces the teeth, are efficient in the toothbrushing operation in the direction away from the edge of the gums towards the free end of the teeth. This differs from what is the case with toothbrushes with aligned brush head and handle where the toothbrush must be inclined for the brushing operation, which means that the brushing surface defined by the points of the bristles is obliquely oriented in the mouth with respect to the edge of the gums, whereby the bristles on the toothbrush head which are proximal to the hand of the user can hardly reach the very critical areas to be brushed at the transition between the edge of the gums and the teeth.

A material aspect of tooth-brushing is the direction of rotation of the brush. In fact, to achieve efficient toothbrushing it is preferred that the toothbrush head is rotated in such a direction that the bristles sweep over the tooth surfaces away from the edge of the gums towards the free end of the teeth. In order to ensure automatic adjustment of the cylindrical tooth brush head 26 of the toothbrush according to FIG. 3 for such a preferred sweeping direction, irrespective of where in the oral cavity the teeth are to be brushed, the toothbrush is provided with a device determining the preferred sweeping direction. In the shown embodiment, this device has two rotatable, superposed toothed wheels, 29, 30 which are mounted each in a recess in the housing 15 and which in their central portions have a profiled central opening for engagement with a similarly profiled portion 31 of the shaft 16a. The teeth of the toothed wheels 29, 30 are adapted each to cooperate with a fixed tooth 29a, 30a on the lateral wall of the recesses accommodating the toothed wheels. The teeth 29a, 30a and the teeth of the wheels 29, 30 are designed in a ratchet-like arrangement so that they allow rotation of the toothed wheel 29 only in one direction with respect to housing 15 and rotation of the toothed wheel 30 only in the opposite direction with respect to housing 15. The toothed wheels 29 and 30 are arranged in a conventional ratchet and pawl configuration. FIG. 7 shows the arrangement of toothed wheel 30 with a pawl 30a. The shaft portion 31 is designed to be temporarily engaged with one of the toothed wheels 29, 30. The brush head holder 25 is rotatably mounted on the bearing portion 23 of the reciprocating means 20, and a rod 32 spaced from the shaft 16b is fixedly connected to the holder 25. However, the rod 32 is movable in the arcuate slot in portion 23. The rod 32 extends into the housing 15, is rotatable therein and has a profiled oblique cam surface 33 on its free end. The cam surface 33 cooperates with a pin 34 laterally projecting from the member 28 mounted in the housing 15 for longitudinal sliding movement, to cause said pin and thus the shaft 16a to move, as seen in the drawing FIG. 9, upwards or downwards along the cam surface according to the direction of rotation of the rod 32, from a neutral position where the pin 34 contacts the central portion of the cam surface 33, as seen in the direction of inclination of the cam surface. By rotation of the holder 25, the shaft portion 31 can be caused to move from a neutral position, shown, between the toothed wheels 29, 30 into engagement with either of the toothed wheels, according to the direction of rotation of the holder 25.

Consequently, when a force is exerted on one side of the brush 26 (perpendicular to the plane of the drawing), the holder 25, together with the rod 32 connected thereto, can rotate about the shaft portion 16b with respect to the housing 15. During this rotation, a first cam surface on the rod portion 33 acts on the pin 34 for downward movement thereof, thus also causing the element 28 and the shaft portions 16c, 16a connected thereto to move downwards.

A spring 35 biased in said neutral position of the pin 34 is adapted to return the shaft 16a from a position in which the shaft portion 31 engages the lower toothed wheel 29, to the neutral position in which the shaft portion 31 is located between the toothed wheels 29, 30 and to drive the shaft 16a from a neutral position to a position in which the shaft portion 31 engages the upper toothed wheel 30.

To ensure movement of the cam surface 33 so as to permit the above-defined movements of the shaft 16a, there is provided a recess 37 in the housing (FIG. 5) which accommodates a T-shaped projection 38 which laterally protrudes perpendicularly from the rod 32, the recess 37 having arcuate portions 37a which extend in opposite directions from a portion arranged for the leg of the T, and each of which contains a spring 39 and which are adapted to receive the respective side flange 38a of the T-shaped projection 38, according to the direction of rotation of the rod 32. The springs 39 counteract the movement of the side flanges 38a of the T-shaped projection into the arcuate portions 37a and thus tend to return the T-shaped projection 38 to the neutral position in which the T-shaped projection is shown in FIG. 5. The recess 37 in the housing 15 is large enough in the vertical direction as shown in FIG. 3 to accommodate projection 38 when rod 32 moves longitudinally relative to housing 15. The cam surface 33 is configured so that longitudinal movement of rod 32 does not also move member 28 in the longitudinal direction. Further, member 28 does not experience any rotational movement at any time. However, the cam surface 33 is configured so that rotational movement of rod 32 about axis 16 will cause movement of member 28 in the longitudinal direction. Therefore only rotational movement, and not longitudinal movement, of rod 32 will cause member 28 to move longitudinally.

Further, the shaft 16a fixedly carries a disk 40 which serves to allow rotation of the brush to a value corresponding to one revolution of disc 40. Thus if the transmission arrangement of 27a, 27b and 27c rotates the brush 26 twice for each revolution of shaft 16 and disc 40, the brush 26 will only rotate twice, and then disc 40 will return to its neutral position, assuming no force is exerted on the side of the brush. Disc 40 has a profiled i.e. non circular periphery and which, during said movement of the shaft 16a to and from the neutral position, moves in a recess 41 in the housing 15, the disk 40 in a neutral position engaging the inner edge surface, facing the shaft 16a, of a flange 42 projecting from the lateral boundary wall of the recess 41, which edge surface is profiled in a way corresponding to the peripheral profile of the disk 40. Disc 40 has a non-circular profiled periphery of a certain configuration. The edge surface of the flange 42 also has a configuration similar to that of disc 40. Therefore, disc 40 may pass from one recess portion 41a to another recess portion 41b only when shaft 16a is in a particular rotational position. Thus, the flange 42 is arranged to allow the disk 40 to pass to countersunk recess portions 41a, 41b on either side of the flange 41 in only one position of the disk 40 during one revolution thereof. FIG. 3 shows this position of passage of the flange, which corresponds to the neutral position of the disk 32.

Disc 40, when urged downwards into the recess 41a under the action of the cam surface 33, can be rotated one revolution in this recess 41a, and thereafter, i.e. when the inner periphery of the flange 42 and the outer periphery of the disc 40 are aligned, disc 40 will be pressed, under the action of spring 35, into the opening defined by the flange 42. Similar action occurs when the brush head is rotated in the other direction whereupon the disc 40 is urged upwards into the recess 41b.

The spring constants of the springs 35 and 39 are so selected that when the T-projection 38 is in its neutral center position, the cam surface 33 is also in its neutral center position, the shaft portion 31 is also in its neutral center position between the two toothed wheels 29 and 30 and the disk 40 is in its neutral center position between recesses 41a and 41b. When the holder 25 is turned in one direction, the shaft 16a is moved downwards, this being made possible because the disk 40 was in a neutral position as stated above. The disk 40 is held in the recess portion 41a and, when rotated by means of the operating member 10, can perform one revolution in the direction determined by the lower toothed wheel 29 which now engages the shaft portion 31. After one revolution the disk 40, by the intermediary of the spring 35 and the spring 39, is returned to the neutral position. When the holder 25 is turned in the opposite direction, the shaft 16a is moved upwards by the intermediary of the spring 35, the disk 40 being held in the recess portion 41b and, when rotated by means of the operating member 10, being able to perform one revolution in the opposite direction with respect to the previous direction in that the shaft portion 31 engages the upper toothed wheel 30, whereupon the disk 40 by the intermediary of the corresponding spring 39, is returned to neutral position. Of course, if force is applied to the proper side of the brush at the end of one revolution of shaft 16a, member 28 will be longitudinally displaced and the springs 24 and 39 will not force disc 40 back to the neutral center position, but will instead allow disc 40 to remain in its existing position, to allow further rotation of the brush. The rotation of the brush head holder 25 is effected in that the toothbrush head 26 is gently pressed against the tooth surfaces, so that the holder is turned with respect to the housing 15, and the above described engagements, determining the direction of rotation of the brush head, between the cam surface 33 and the pin 34, and between the shaft portion 31 and the respective toothed wheel 29, 30 take place. The aforesaid, desired direction of sweeping or rotation of the brush head 26 is easily determined by placing the respective toothed wheel 29, 30 in the correct recess therefor. If use is made of the correct toothed wheel 29, 30 with regard to the desired direction of sweeping, the correct sweeping direction of the toothbrush head is always had, i.e. from the gums to the free ends of the teeth, and the brushhead is blocked against rotation in the opposite direction. As is evident, this occurs irrespective of where in the oral cavity brushing is effected when the toothbrush is so held that the side of the brush head 26 facing away from the handle is directed towards the area of attachment of the teeth in the upper and lower jaws. Such a correct brushing direction is achieved in the embodiment in FIG. 3 if the lower toothed wheel 29 is arranged to allow left-hand rotation and to block against right-hand rotation, and if the upper toothed wheel 30 is arranged to permit right-hand rotation and to block against left-hand rotation.

Another important aspect of correct tooth-brushing is the time during which the tooth-brushing is carried out in each jaw area subjected to brushing. This time must not be too short. This aspect has been considered in the invention and has previously been touched upon. In fact, one revolution of the toothbrush head has proved sufficient to obtain satisfactory brushing on the jaw area subjected to brushing. In the described arrangement using the disk 40, precisely one revolution of the toothbrush head is performed. If said slight pressure of the toothbrush head is maintained against the teeth after the brush head has performed one revolution, such that the disk 40 does not return to its neutral position, the brush head will go on rotating in the desired direction, which, of course, is no disadvantage. In order to give the user an indication that one revolution has been completed, i.e. that sufficient brushing has been effected on the contemplated area of the jaw, appropriate indicator means can be provided in the toothbrush, which may for instance be flexible, partially overlapping tongues on the free periphery of the flange 42 and the periphery of the disk 40, which tongues are adapted to emit an audible click when the disk 40 moves to neutral position. It should be pointed out that toothbrushing with the brush of the invention gives essential advantages as compared with the rubbing method and in particular the conventional rotary sweeping method. An advantageous effect is that by rotating the rotor 6 or the operating member 10 only with the fingers, it is possible to obtain a rotary movement as well as a reciprocating movement of the toothbrush head, i.e. a simultaneous combination of rubbing and rotary sweeping. Another advantageous effect is gained in that the bristles, by the rotation of the brush head, are first rotated against the gums. At the transition from the gums to the teeth, there is a concavity entailing that the pressure on the bristles, as they move from the gums and into the concavity, will reduce and the bristles gather in the concavity to occupy an advantageous angle for performing a rubbing motion, resulting from the reciprocation of the brush head, in the concavity critical from the point of view of dental hygiene.

I claim:

1. A toothbrush comprising:
an elongated handle;
a cylindrical brush portion extending from the end of said handle and having first and second sides;
wherein said handle includes brush control and rotating means, connected to said brush portion and including a rotating rotor member, for rotating the brush portion in a first direction about its longitudinal axis in response to rotation of said rotor member and when force is exerted on the first side of said brush portion, and for rotating the brush portion in a second direction about its longitudinal axis in a response to rotation of said rotor member and when force is exerted on the second side of said brush portion, and for reciprocating said brush portion, during rotation thereof, in its axial direction relative to said rotor member in response to rotation of said rotor member.

2. Toothbrush as claimed in claim 1 wherein the longitudinal axis of the brush portion is offset with respect to the longitudinal axis of the handle.

3. Toothbrush as claimed in claim 1, wherein the handle comprises an upper portion and a lower portion and wherein the upper portion is rotatably mounted with respect to the lower portion of the handle about the longitudinal axis thereof and wherein the brush control and rotating means comprises means, spaced from the longitudinal axis of the handle, for setting said brush control and rotating means in one or the other rotational direction according to the direction of rotation of said upper portion of the handle, as determined by the direction of force exerted on the brush portion.

4. Toothbrush as claimed in claim 1, wherein said brush control and rotating means comprises a toothed wheel and toothed belt transmission in said upper portion of the handle, and a shaft connected to said transmission and extending along the longitudinal axis of the handle and further connected to said rotor member; and wherein said rotor member is provided in the lower portion of the handle.

5. Toothbrush as claimed in claim 4, wherein said setting means comprises a cam whose surface engages said shaft for moving said shaft along its longitudinal axis in a direction, in accordance with the direction of rotation of said upper portion of the handle, and wherein said shaft has a profiled portion which selectively engages two toothed wheel/locking means for permitting rotation of the rotor member and brush portion in relatively opposite directions.

6. Toothbrush as claimed in claim 4 wherein the brush control and rotating means comprises a telescopic joint in said shaft, and an undulatory surface on said rotor member which cooperates with a mating undulatory surface disposed longitudinally displaceable in the lower portion of the handle and connected to said upper rotatable portion of the handle, whereby rotation of the rotor member will cause the mating undulatory surfaces to rotate with respect to each other and effect reciprocation of the brush portion with respect to the lower portion of the handle.

7. Toothbrush as claimed in claim 1 wherein said brush control and rotating means restricts the rotation of the brush portion to one revolution.

* * * * *